(12) United States Patent
Harimoto et al.

(10) Patent No.: US 11,155,785 B2
(45) Date of Patent: Oct. 26, 2021

(54) INCUBATED PLATELET CONCENTRATION MODULE AND METHOD FOR PRODUCING PLATELET PREPARATION USING SAME

(71) Applicant: Toray Industries, Inc., Tokyo (JP)

(72) Inventors: Kenichi Harimoto, Otsu (JP); Hirokazu Sakaguchi, Otsu (JP); Kota Hatta, Otsu (JP); Kazuhiro Tanahashi, Otsu (JP)

(73) Assignee: Toray Industries, Inc.

( * ) Notice: Subject to any disclaimer, the term of this patent is extended or adjusted under 35 U.S.C. 154(b) by 141 days.

(21) Appl. No.: 16/338,065

(22) PCT Filed: Sep. 25, 2017

(86) PCT No.: PCT/JP2017/034458
§ 371 (c)(1),
(2) Date: Mar. 29, 2019

(87) PCT Pub. No.: WO2018/062073
PCT Pub. Date: Apr. 5, 2018

(65) Prior Publication Data
US 2020/0024575 A1    Jan. 23, 2020

(30) Foreign Application Priority Data

Sep. 30, 2016    (JP) .............................. JP2016-193154

(51) Int. Cl.
*C12N 5/078* (2010.01)
*B01D 63/02* (2006.01)
(Continued)

(52) U.S. Cl.
CPC ........... *C12N 5/0644* (2013.01); *B01D 63/02* (2013.01); *B01D 69/081* (2013.01); *B01D 71/68* (2013.01);
(Continued)

(58) Field of Classification Search
CPC ................ C12N 5/0644; C12N 5/0068; C12N 2533/30; B01D 63/02; B01D 69/081;
(Continued)

(56) References Cited

U.S. PATENT DOCUMENTS 3,373,876 A    3/1968  Stewart
4,787,974 A   11/1988  Ambrus et al.
(Continued)

FOREIGN PATENT DOCUMENTS

EP    2335814 A1    6/2011
JP    5415476 A     2/1979
(Continued)

OTHER PUBLICATIONS

International Search Report and Written Opinion for International Application No. PCT/JP2017/034458, dated Dec. 26, 2017—7 pages.

(Continued)

*Primary Examiner* — Liam Royce
(74) *Attorney, Agent, or Firm* — RatnerPrestia

(57) ABSTRACT

The present invention provides a hollow fiber membrane module which makes it possible to concentrate incubated platelets by efficiently removing water from an incubated platelet suspension liquid containing incubated platelets while suppressing deterioration of the function of the incubated platelets. The present invention provides an incubated platelet concentration module in which a plurality of hollow fiber membranes each having pores with an average pore diameter of 2 μm or less on a surface of the hollow fiber membrane are packed in a casing having at least one inlet for supplying an incubated platelet suspension liquid before concentration into the hollow fiber membranes, wherein a value (X/Y1) obtained by dividing a total cross-sectional (Continued)

area (X) of the plurality of hollow fiber membranes by a total cross-sectional area (Y1) of the least one inlet is 4.0 or less.

6 Claims, 1 Drawing Sheet

(51) Int. Cl.
  *B01D 69/08* (2006.01)
  *B01D 71/68* (2006.01)
  *B01D 71/38* (2006.01)
  *B01D 71/62* (2006.01)
  *C12M 1/00* (2006.01)

(52) U.S. Cl.
  CPC ............... *B01D 71/38* (2013.01); *B01D 71/62* (2013.01); *B01D 2311/14* (2013.01); *B01D 2313/20* (2013.01); *B01D 2313/243* (2013.01); *B01D 2325/02* (2013.01); *B01D 2325/20* (2013.01); *C12M 29/16* (2013.01)

(58) Field of Classification Search
  CPC ........ B01D 71/68; B01D 71/38; B01D 71/62; B01D 2311/14; B01D 2313/20; B01D 2313/243; B01D 2313/10; B01D 2325/02; B01D 2325/20; B01D 61/18; C12M 29/06; A61M 1/3496; A61M 1/34; A61K 35/19
  See application file for complete search history.

(56) References Cited

U.S. PATENT DOCUMENTS

| | | | |
|---|---|---|---|
| 2011/0065190 A1 | 3/2011 | Nakano et al. | |
| 2013/0288370 A1* | 10/2013 | Humes | B01D 63/02 435/375 |
| 2015/0053609 A1 | 2/2015 | Osabe et al. | |
| 2015/0165106 A1* | 6/2015 | Buck | A61M 1/165 210/321.8 |
| 2015/0204767 A1* | 7/2015 | Taniguchi | B01D 69/081 435/374 |
| 2016/0074569 A1 | 3/2016 | Schuetz et al. | |
| 2016/0339159 A1 | 11/2016 | Nosaka et al. | |

FOREIGN PATENT DOCUMENTS

| | | |
|---|---|---|
| JP | 61238834 A1 | 10/1986 |
| JP | 62290469 A | 12/1987 |
| JP | 0347268 A | 2/1991 |
| JP | 09108338 A | 4/1997 |
| JP | 2888607 B2 | 5/1999 |
| JP | 2000334277 A | 12/2000 |
| JP | 2007089432 A | 4/2007 |
| JP | 2012143554 A | 8/2012 |
| JP | 2015150349 A | 8/2015 |
| JP | 2016116465 A | 6/2016 |
| JP | 2016190824 A | 11/2016 |
| WO | 2009139177 A1 | 11/2009 |
| WO | 2012051595 A1 | 4/2012 |
| WO | 2013147001 A1 | 10/2013 |
| WO | 2015125852 A1 | 8/2015 |

OTHER PUBLICATIONS

Ogawa, M., "Differentiation and Proliferation of Hematopoietic Stem Cells", Blood, vol. 81, No. 11, Jun. 1, 1993—pp. 2844-2853.
Takayama et al., "Generation of Functional Platelets from Human Embryonic Stem Cells In Vitro Via ES-sacs, VEGF-promoted Structures that Concentrate Hematopoietic Progenitors", Blood, vol. 111, No. 11, Jun. 1, 2008—pp. 5298-5306.
Extended European Search Report for European Application No. 17 856 026.4, dated Apr. 29, 2020, 10 pages.

* cited by examiner

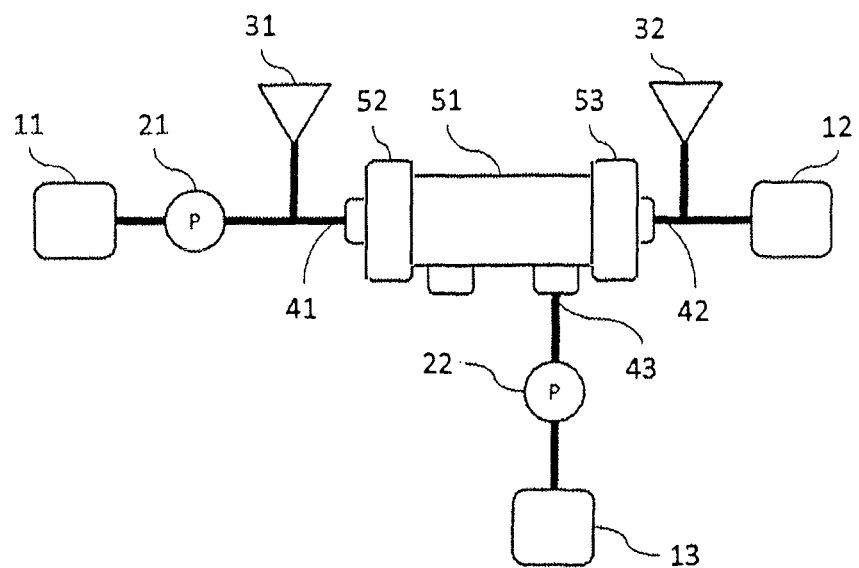

INCUBATED PLATELET CONCENTRATION MODULE AND METHOD FOR PRODUCING PLATELET PREPARATION USING SAME

CROSS REFERENCE TO RELATED APPLICATIONS

This is the U.S. National Phase application of PCT/JP2017/034458, filed Sep. 25, 2017, which claims priority to Japanese Patent Application No. 2016-193154, filed Sep. 30, 2016, the disclosures of these applications being incorporated herein by reference in their entireties for all purposes.

FIELD OF THE INVENTION

The present invention relates to an incubated platelet concentration module and a method for producing a platelet preparation using the module.

BACKGROUND OF THE INVENTION

Currently, all platelet preparations to be used for blood transfusion are produced from blood components collected from donated blood. However, since there may be a shortage of donors with the advent of an aging society, research and development is conducted on production of incubated platelet preparations which are not dependent on donated blood. Examples of the method for obtaining incubated platelets include an incubation method in which platelets are produced from hematopoietic stem cells derived from bone marrow or umbilical cord blood (Non-Patent Document 1), and an incubation method in which platelets are produced from pluripotent stem cells (Non-Patent Document 2). In either of the methods, the number of platelets required for single blood transfusion is exceptionally large (about 200 billion), and therefore incubation on a scale of several tens of liters to several hundreds of liters is essential. On the other hand, since the volume of an infusion to be administered in single transfusion is several hundreds of milliliters, a step of concentrating incubated platelets is essential for production of an incubated platelet preparation. In this specification, the term "incubated platelets" refers to platelets prepared by a production process including an incubation step in vitro.

Currently, a centrifugation method is mainly used for concentrating platelets derived from whole blood, but when treatment of a large amount of liquid is necessary as in concentration of incubated platelets, the treatment time is so that the function of platelets is easily deteriorated under the load of centrifugation, and therefore it is practically impossible to apply this method.

On the other hand, a method using a hollow fiber membrane module has been heretofore used for separating erythrocytes and plasma (Patent Documents 1 and 2). As hollow fiber membranes to be applied to such a method, improved techniques have been developed, such as a porous membrane of a polysulfone-based resin which is hardly clogged and soiled (Patent Document 3), and a membrane, the durability of which is improved by spinning a stock solution including a polysulfone-based polymer and a hydrophilic polymer (Patent Document 4). Further, a technique for purifying plasma components from a platelet suspension liquid derived from donated blood has also been developed (Patent Document 5).

Patent Documents

Patent Document 1: Japanese Patent Laid-open Publication No. 62-290469
Patent Document 2: Japanese Patent Laid-open Publication No. 54-15476
Patent Document 3: Japanese Patent Laid-open Publication No. 61-238834
Patent Document 4: Japanese Patent Laid-open Publication No. 2000-334277
Patent Document 5: Japanese Patent Laid-open Publication No. 2012-143554

Non-Patent Documents

Non-Patent Document 1: BLOOD, 1 Jun. 1993 VOL. 81, No. 11 p2844-2853
Non-Patent Document 2: BLOOD, 1 Jun. 2008 VOL. 111, No. 11 p5298-5306

SUMMARY OF THE INVENTION

Thus, mention is made of a method in a step of concentrating incubated platelets, platelets are concentrated by removing an incubation liquid using a hollow fiber membrane. The hollow fiber membrane makes it possible to deal with massive treatment because the number and length of hollow fiber membranes to be placed in a module can be easily adjusted according to the amount of liquid to be treated.

However, incubated platelets are exposed to an incubation environment unsuitable for preservation of platelets for a long time, and are more easily deteriorated as compared to platelets of donated blood which are produced in a short time after blood collection, and preserved in a suitable environment. Thus, there is the problem that in removal of an incubation liquid using a hollow fiber membrane, incubated platelets are broken, so that the function is deteriorated:

An object of the present invention is to provide a hollow fiber membrane module which makes it possible to concentrate incubated platelets by efficiently removing water from an incubated platelet suspension liquid containing incubated platelets while suppressing deterioration of the function of the incubated platelets.

That is, the present invention provides an incubated platelet concentration module in which a plurality of hollow fiber membranes each having pores with an average pore diameter of 2 μm or less on a surface of the hollow fiber membrane are packed in a casing having at least one inlet for supplying an incubated platelet suspension liquid before concentration into the hollow fiber membranes, wherein a value (X/Y1) obtained by dividing a total cross-sectional area (X) of the plurality of hollow fiber membranes by a total cross-sectional area (Y1) of the at least one inlet is 4.0 or less; and a method for producing a platelet preparation including a step of concentrating incubated platelets using the module.

According to the present invention, a liquid can be removed from an incubated platelet suspension liquid without deteriorating incubated platelets, so that it is possible to efficiently concentrate the incubated platelet suspension liquid while maintaining high quality.

BRIEF DESCRIPTION OF THE DRAWING

The FIG. is a schematic view of a concentration apparatus using an incubated platelet concentration module of the present invention.

DETAILED DESCRIPTION OF EMBODIMENTS OF THE INVENTION

Hereinafter, an incubated platelet concentration module of the present invention will be described. An embodiment of the present invention may be described in part with reference to the drawing, but the present invention is not limited to the illustrated embodiment.

The average pore diameter of pores present on a surface (hereinafter, sometimes referred to simply as an "average pore diameter") of a hollow fiber membrane packed in the incubated platelet concentration module (hereinafter, sometimes referred to simply as a "module") of the present invention is 2 µm or less because the size of a human platelet is 3 to 4 µm. Here, the "surface" of a hollow fiber membrane refers to both of an "outer surface" which is an outside surface of a hollow fiber membrane molded in a straw shape, and an "inner surface" which is an inside surface of a straw-shaped hollow fiber membrane. When the average pore diameter is larger as compared to the size of a human platelet, platelets make an entrance into pores of the hollow fiber membranes, so that clogging occurs, leading to reduction of water removal efficiency, and also, the number of platelets passing through the module decreases, leading to marked reduction of the recovery ratio. In addition, when the average pore diameter is equivalent to the size of a human platelet, platelets close pores present on the inner surface of the hollow fiber membranes, so that water removal efficiency is reduced, and also, elimination of closing may cause deterioration of platelets. When the average pore diameter is 2 µm or less, a cake layer is stacked on a surface of the hollow fiber membrane, resulting in reduction of water removal efficiency, but such a cake layer can be often removed without deteriorating platelets.

In the incubated platelet concentration module of the present invention, a plurality of hollow fiber membranes as described above are packed in a casing. The casing has at least one inlet for supplying a liquid to the inside of the hollow fiber membrane and at least one outlet for letting out the liquid from the inside of the hollow fiber membrane. A value (X/Y1) obtained by dividing the total cross-sectional area (X) of the hollow fiber membrane by the total cross-sectional area (Y1) of the at least one inlet is set to 4.0 or less. Preferably, a value (X/Y2) obtained by dividing the total cross-sectional area (X) of the hollow fiber membrane by the total cross-sectional area (Y2) of the at least one outlet is also set to 4.0 or less.

The hollow fiber membrane module shown in the FIG. has a tubular casing 51, and headers 52 and 53 connected and fixed to both ends of the casing 51, respectively, an inlet 41 for supplying an incubated platelet suspension liquid before concentration into the hollow fiber membrane is protrusively formed at the top of the header 52, and an outlet 42 for letting out the concentrated incubated platelet suspension liquid after passing through the inside of the hollow fiber membrane is protrusively formed at the top of the header 53. Further, at the side part of the casing 51, a discharge port 43 for discharging a waste liquid exuded outside the hollow fiber membrane by passing through the pores on the surface of the hollow fiber membrane from the inside of the hollow fiber membrane is formed.

A plurality of hollow fiber membranes are arranged in a bundle shape over the entire length in a long axis direction in the tubular casing 51. Both ends of the hollow fiber membrane are fixed to the inner peripheral surface of the casing 51 by a header 52-side partition wall and a header 53-side partition wall formed of a cured potting agent in such a manner that an inner cavity of the hollow fiber membrane is not closed. The number of hollow fiber membranes retained in the module is not particularly limited, but is preferably 400 or more, more preferably 1000 or more, still more preferably 2500 or more, even more preferably 4000 or more because the volume of the platelet suspension liquid to be concentrated is several tens of liters to several hundreds of liters as described above.

The cross-sectional area of the hollow fiber membrane is an area of an inner circle of the straw-shaped hollow fiber membrane cut into a round shape, and is calculated by the following equation.

hollow fiber membrane cross section=π(hollow fiber membrane inner diameter/2)$^2$ (π=circular constant)

Here, the thickness of each of 16 hollow fiber membranes randomly selected in the module is measured by a 1000-power lens of a micro-watcher (e.g. VH-Z 100 from KEYENCE Corporation), an average thereof is determined, and the hollow fiber membrane inner diameter is calculated from the following equation. The hollow fiber membrane outer diameter is an average of values determined by measuring the outer diameters of randomly selected 16 hollow fiber membranes by a laser displacement meter (e.g. LS 5040 T from KEYENCE Corporation).

hollow fiber membrane inner diameter=hollow fiber membrane outer diameter−2×average of thickness The total cross-sectional area (X) of the hollow fiber membranes is a sum of cross-sectional areas of a plurality of hollow fiber membranes appearing in a cross-section obtained by cutting the module in a direction perpendicular to the fiber axis direction of the hollow fiber membranes.

The cross-sectional area of the inlet or the cross-sectional area of the outlet is an area of a cross-section obtained by cutting the narrowest part of the inlet or the outlet perpendicularly to the flow direction. For example, when the inlet or the outlet is a cylinder, the cross-sectional area of the inlet or the cross-sectional area of the outlet is an area of a circle which is calculated from the inner diameter of the cylinder. The total cross-sectional area (Y1) of the inlet or the total cross-sectional area (Y2) of the outlet is the cross-sectional area of the inlet or the outlet when there is one inlet or outlet, and the sum of cross-sectional areas of inlets or outlets when there are a plurality of inlets or outlets.

Incubated platelets are more vulnerable to a change in pressure than platelets of donated blood, and when there is a large difference between the total cross-sectional area of hollow fiber membranes and the total cross-sectional area of inlets or outlets, a change in pressure during the process easily increases, leading to deterioration of platelets. Thus, the value (X/Y1) obtained by dividing the total cross-sectional area (X) of hollow fiber membranes by the total cross-sectional area (Y1) of inlets is preferably 4.0 or less, more preferably 2.0 or less, most preferably 0.8 or more and 1.2 or less. Similarly, the value (X/Y2) obtained by dividing the total cross-sectional area (X) of hollow fiber membranes by the total cross-sectional area (Y2) of outlets is preferably 4.0 or less, more preferably 2.0 or less, most preferably 0.8 or more and 1.2 or less.

In addition, in the module of the present invention, the total membrane area of hollow fiber membranes contained in the module is preferably 0.1 m$^2$ or more and 1 m$^2$ or less.

The total membrane area (Z) of hollow fiber membranes refers to an area of the inside surface of the hollow fiber membrane, and is determined by the following equation.

inner surface area of hollow fiber membrane=π× hollow fiber membrane inner diameter×effective length Here, the effective length is a length obtained by subtracting the length of a part, on which a potting material is deposited, from the total length of the hollow fiber membrane packed in the hollow fiber membrane module, i.e. the length of a part which can actually function in concentration of platelets. The total membrane area (Z) of hollow fiber membranes is a sum of the inner surface areas of the hollow fiber membranes packed in the module, and is calculated from the following equation when the hollow fiber membranes are uniform.

> total membrane area of hollow fiber membranes=inner surface area of hollow fiber membrane×number of hollow fiber membranes When the number of platelets to be treated increases with respect to the total membrane area (Z) of hollow fiber membranes, the cake layer deposited on the membrane surface becomes thicker, so that platelets are easily deteriorated. The total membrane area (Z) of hollow fiber membranes packed in the module is preferably 0.1 m² or more. On the other hand, the total membrane area of hollow fiber membranes is preferably 1.0 m² or less for preventing the cake layer from being widely stacked on the membrane surface, resulting in reduction of the platelet recovery ratio.

The total cross-sectional area (X) of hollow fiber membranes have an influence on the linear velocity of the liquid passing through the inside of the hollow fiber membrane (membrane intracavity passage linear velocity), and the total membrane area (Z) of hollow fiber membranes has an influence on the linear velocity of the liquid passing from the inside to the outside of the hollow fiber membrane (membrane surface passage linear velocity). The influences are expressed by the following equations.

> membrane intracavity passage linear velocity=inflow flow rate÷total cross-sectional area (X) of hollow fiber membranes > membrane surface passage linear velocity=discharge flow rate÷total membrane area (Z) of hollow fiber membranes When the membrane intracavity passage linear velocity is low, a cake layer with platelets stacked on the surface of the hollow fiber membrane tends to be easily formed, leading to deterioration of the function of the module. Since the number of platelets that can be recovered by passing through the module decreases due to formation of the cake layer, and further it is normal platelets that form the cake layer, recovered platelets include a large number of platelets having a relatively deteriorated function. When the inflow flow rate is increased, or the total cross-sectional area (X) of hollow fiber membranes is decreased for increasing the membrane intracavity passage linear velocity, a change in pressure increases, so that platelets are easily deteriorated. Thus, the total cross-sectional area of hollow fiber membranes is preferably 2 cm² or more and 10 cm² or less, more preferably 2 cm² or more and 5 cm² or less.

When the membrane surface passage linear velocity is increased with respect to the membrane intracavity passage linear velocity, platelets are stacked on the surface of the hollow fiber membrane, so that a cake layer tends to be easily formed, leading to deterioration of the function of the module and reduction of the number of platelets that can be recovered by passing through the module. Further, since the cake layer is formed on the surface of the hollow fiber membrane mainly by normal platelets, i.e. annexin-negative platelets, recovered platelets include a large number of platelets having a relatively deteriorated function, i.e. annexin-positive platelets. The inflow flow rate and the outflow flow rate can also be increased or decreased for adjusting the membrane intracavity passage linear velocity and the membrane surface passage linear velocity, but in this case, a sufficient concentration ratio is hardly achieved. Thus, the value (X/Z) obtained by dividing the total cross-sectional area (X) of hollow fiber membranes by the total membrane area (Z) of hollow fiber membranes is preferably 0.0005 or less, more preferably 0.0004 or less.

Preferably, the hollow fiber membrane to be used for the incubated platelet concentration module of the present invention has a water permeability of 30 mL/hr/Pa/m² or more. When the water permeability of the hollow fiber membrane is less than 30 mL/hr/Pa/m², water removal efficiency may be reduced, or platelets may be easily activated.

The hollow fiber membrane to be used for the incubated platelet concentration module of the present invention is preferably a polysulfone-based hollow fiber membrane. The "polysulfone-based hollow fiber membrane" refers to a hollow fiber membrane formed with a polysulfone-based polymer as a main raw material (raw material occupying 50% by mass or more of all raw materials). Here, the "polysulfone-based polymer" refers to a polymer having an aromatic ring, a sulfonyl group and an ether group in the main chain thereof.

Examples of the polysulfone-based polymer include polysulfone represented by the following general formula (I), polysulfone represented by the following general formula (II), polyethersulfone, and polyallyl ether sulfones, and the polysulfone-based polymer is preferably polysulfone represented by the general formula (I) or polysulfone represented by the general formula (II), more preferably polysulfone in which the value of n is 50 to 80. The "polysulfone-based polymer" also includes block copolymers of polysulfone represented by the general formula (I), or the like and other monomer, and modified products such as a polysulfone represented by the general formula (I). The structure derived from the "other monomer" in the block copolymer of polysulfone represented by the general formula (I), or the like and other monomer is preferably 10% by mass or less based on the total amount of the block copolymer.

[Chemical Formula 1]

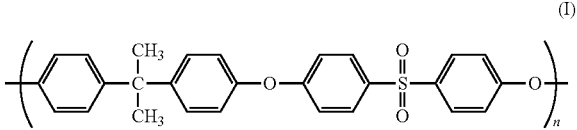

[Chemical Formula 2]

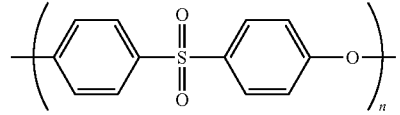

More specific examples of the polysulfone include Udel (registered trademark) Polysulfone P-1700 and P-3500 (manufactured by Solvay), Ultrasone 53010 and 56010 (BASF SE), Radel A (Solvay) and Ultrason E (BASF SE).

Preferably, the hollow fiber membrane to be used for the incubated platelet concentration module of the present invention has a hydrophilic polymer carried on the inner surface. The phrase "a hydrophilic component is carried on the inner surface of the hollow fiber membrane" refers to not only a case where a hydrophilic polymer is covalently bonded to the inner surface of the hollow fiber membrane, but also a state in which the hydrophilic polymer is fixed to the inner surface of the hollow fiber membrane in some form.

The hydrophilic polymer is a water-soluble polymer compound, or a polymer that is water-insoluble, but interacts with water molecules through an electrostatic interaction or a hydrogen bond. Examples of the hydrophilic polymer include homopolymers having methacrylic acid, acrylic acid, itaconic acid, 2-hydroxyethyl methacrylate, 2-hydroxyethyl acrylate, 2-hydroxypropyl methacrylate, 2-hydroxypropyl acrylate, glycerol methacrylate, polyethylene glycol methacrylate, N,N'-dimethylacrylamide, N-methylacrylamide, dimethylaminoethyl methacrylate, methylenebisacrylamide, diacetoneacrylamide, vinylpyrrolidone, vinyl alcohol, ethylene glycol or propylene glycol as a monomer; and copolymers containing at least one of these compounds as a monomer, and polyvinylpyrrolidone (PVP) which is a polymer of vinylpyrrolidone, copolymers of vinylpyrrolidone and vinyl acetate, and copolymers of vinyl acetate and vinyl caprolactam are preferable.

The abundance ratio of the hydrophilic polymer on the inner surface of the hollow fiber membrane is preferably 30 to 60%. The abundance ratio of the hydrophilic polymer on the inner surface of the hollow fiber membrane can be determined by a measured value of hydrophobic polymer-specific atoms and a measured value of hydrophilic polymer-specific atoms, which are obtained by measuring the inner surface of the hollow fiber membrane by X-ray photoelectron spectroscopy (XPS).

For example, when the hydrophobic polymer is polysulfone, and the hydrophilic polymer is polyvinylpyrrolidone, the abundance ratio of the hydrophilic polymer can be measured as a content ($R_{VP}$) (mass %) of a vinylpyrrolidone unit on the inner surface of the hollow fiber membrane. That is, from a measured value ($R_N$) (atom %) of the amount of nitrogen derived from the vinyl pyrrolidone unit and a measured value ($R_S$) (atom %) of the amount of sulfur derived from the sulfone group of polysulfone, $R_{VP}$ (mass %) on the inner surface of the hollow fiber membrane can be calculated in accordance with the following equation. Here, the molecular weight of the vinylpyrrolidone unit is 111, and the molecular weight of the repeating unit forming polysulfone is 442.

$$R_{VP}=(R_N\times111)/(R_N\times111+R_S\times442)\times100$$

When there is no specific atom, $R_{VP}$ can be calculated from a measured value of a functional group measured by XPS. For example, when the hydrophilic polymer is a vinylpyrrolidone-vinyl acetate copolymer, $R_{VP}$ can be determined in the manner described below. The molecular weight of the vinyl pyrrolidone unit is 111, the molecular weight of the repeating unit forming polysulfone is 442, and the molecular weight of the vinyl acetate unit is 86. The content ($R_{VA}$) (mass %) of the vinyl acetate unit on the surface is calculated in accordance with the following equation from the values of the amount of nitrogen ($R_N$) (atom %), the amount of sulfur ($R_S$) (atom %), and the amount of carbon derived from the ester group ($R_{Coo}$) (atom %).

content ($R_{VA}$) (mass %) of vinyl acetate on surface of hollow fiber membrane=$(R_{Coo}\times86)/(R_N\times111+R_S\times442+R_{Coo}\times86)\times100$ In addition, the content ($R_{VP}$) (mass %) of vinylpyrrolidone unit on the surface of the hollow fiber membrane is calculated in accordance with the following equation.

$$R_{VP}=(R_N\times111)/(R_N\times111+R_S\times442+R_{Coo}\times86)\times100$$

The abundance ratio of the vinylpyrrolidone-vinyl acetate copolymer on the inner surface of the hollow fiber membrane can be calculated as a sum of the content of vinyl pyrrolidone ($R_{VP}$) and the content of vinyl acetate ($R_{VA}$).

abundance ratio (mass %) of hydrophilic group-containing polymer on inner surface of hollow fiber membrane=$R_{VP}+R_{VA}$ When the abundance ratio of the hydrophilic polymer on the inner surface of the hollow fiber membrane is 30 mass % or more, platelets deposited on the inner surface of the hollow fiber membrane are easily peeled off. The abundance ratio of the hydrophilic polymer on the inner surface of the hollow fiber membrane is more preferably 35 mass %. On the other hand, when the abundance ratio of the hydrophilic polymer on the inner surface of the hollow fiber membrane is 60 mass % or less, a situation can be prevented in which swelling occurs on the inner surface of the hollow fiber membrane due to presence of an excessive amount of the hydrophilic polymer, leading to an increase in filtration resistance.

Examples of the method for carrying a hydrophilic component on the inner surface of the hollow fiber membrane include a method including performing coating by physical adsorption; a method including crosslinking the hydrophilic polymer with the hollow fiber membrane by heat or radiation; and a method including forming a chemical bond between the hydrophilic polymer and the hollow fiber membrane through chemical reaction.

During formation of the hollow fiber membrane, an injection liquid is fed to the inside at the time of discharging a membrane forming stock solution from a double annular die, and when the hydrophilic polymer is added to the injection liquid, the hollow fiber membrane is phase-separated, so that the hydrophilic polymer in the injection liquid is diffused to the membrane forming stock solution side before a membrane structure is determined, and therefore the hydrophilic polymer can be efficiently deposited on the inner surface of the hollow fiber membrane. By performing the heat treatment, radiation treatment, chemical reaction or the like with the hydrophilic polymer deposited on the inner surface of the hollow fiber membrane by the above-mentioned method, the hydrophilic polymer can be easily fixed the inner surface of the hollow fiber membrane.

In the incubated platelet concentration module of the present invention, the turn-to-annexin-positive ratio associated with passage of the incubated platelet suspension liquid before concentration (liquid before treatment) through the module is preferably is 20% or less. The turn-to-annexin-positive means that phosphatidylserine appears on the cell surfaces of incubated platelets contained in the incubated platelet suspension liquid while the incubated platelet suspension liquid passes through the module, and the phosphatidylserine is detected by annexin after passage through the module, and the turn-to-annexin-positive ratio is a difference in annexin-positive ratio before and after passage through the module. A platelet suspension liquid with a high annexin-positive ratio has been reported to accelerate thrombus formation and shorten the circulation time when transfused, and cannot be directly used for production of a preparation. The turn-to-annexin-positive ratio in the module is more preferably 5% or less, and still more preferably 2% or less.

The incubated platelets are deteriorated by a pressure change, and therefore in the incubated platelet concentration module of the present invention, the pressure loss in supply of the liquid from the inlet to the outlet at a flow rate of 2

L/min is preferably 10 kPa or less. The pressure loss in the module is a difference between pressures measured at the inlet and the outlet of the module, and can be measured as follows. A circuit branched perpendicularly to the flow direction is provided immediately before the inlet and immediately after the outlet of the module, and a pressure gauge is installed at the tip of the circuit. Using a roller pump or the like, a liquid before treatment is fed through the module at a flow rate of 2 L/min, a pressure on the inlet side and a pressure on the outlet side are measured, and the pressure loss is determined from the following equation.

pressure loss=pressure on inlet side−pressure on outlet side

The pressure loss in the module is more preferably 5 kPa or less.

A concentrated platelet suspension liquid can be produced by performing cross-flow in which an incubation liquid containing incubated platelets is caused to flow in from the inlet of the incubated platelet concentration module of the present invention, and the liquid is discharged from the outlet at the outside of the hollow fiber membrane. In cross-flow, the concentration ratio can be determined by the flow rate of the liquid before treatment, which is supplied to the module, and the flow rate of the waste liquid discharged from the module. For example, in the case of a concentration module containing hollow fiber membranes with a total membrane area of 1 m², the supply flow rate and the discharge flow rate are preferably 1 L/min and 800 ml/min, respectively, more preferably 500 mL/min and 400 mL/min, respectively for concentrating the incubated platelet suspension liquid by a factor of 5 and achieving a platelet recovery ratio of 80% or more. The liquid component of the concentrated incubated platelet suspension liquid is replaced by a preservation liquid by centrifugation or the like, whereby a platelet preparation can be produced.

EXAMPLES

Hereinafter, the present invention will be described in detail by way of examples, but the present invention is not limited thereto.

Measurement Example 1

Average Pore Diameter

The "average pore diameter of pores present on a surface" was measured and calculated by the following method. First, a 1000-fold image of a surface of a hollow fiber membrane was photographed with a field emission scanning electron microscope (e.g. S-800 from Hitachi, Ltd.). Next, in Matrox Inspector 2.2 (Matrox Electronic Systems Ltd.), image processing was performed in which white portions of pores were turned white, and other portions were turned black, the number of white pores (hereinafter, referred to as "the total number of open pores") and the sum of the numbers of pixels of white pore portions (hereinafter, referred to as a "total area of open pores") were determined, and an average pore diameter per image was calculated in accordance with the following equation 1. The measurement operation was repeated 50 times in total with the operation performed at randomly selected ten points for each of five hollow fibers, and the average for 50 images in total was defined as an "average pore diameter of pores present on a surface". The conditions for photographing the 1000-fold image were as follows.

[Photographing Conditions]
Image size: 655×740 pixels
Image resolution: 0.140845 μm/pixel
Image area S: 9615.2 μm² (square of 92.3 μm (length)× 104.2 μm (width))

average pore diameter (μm)=total open pore area/ total number of open pores     Equation 1

Measurement Example 2

Water Permeability

The water permeability of the hollow fiber membrane was measured and calculated by the following method. First, a hollow fiber membrane was inserted into a plastic tube, and both ends of the hollow fiber membrane were bonded and fixed to the inner walls of both ends of the plastic tube to prepare a module having an effective length of 10 cm. Next, a hydraulic pressure of $1.3×10^4$ Pa was applied from the outside of the hollow fiber membrane, and the amount of water flowing out to the inside of the hollow fiber membrane per unit time was measured, and calculated in accordance with the following equation.

Water permeability (mL/hr/Pa/m²)=QW/(T×P×A)

QW: amount of water flowing out to inside of hollow fiber membrane (mL)
T: time of applying hydraulic pressure (hr)
P: hydraulic pressure (Pa)
A: area of outer surface of hollow fiber membrane (m²)

Measurement Example 3

Abundance Ratio of Hydrophilic Polymer $R_N$, $R_S$ and $R_{coo}$ were each measured by X-ray electron spectroscopy (XPS). Measurement was performed at a measurement angle of 90°, and a region to a depth of about 10 nm from the surface was detected. In addition, an average for three points was used as a measured value.

The measured value $R_{coo}$ was obtained by performing measurement in the following manner. For the amount of carbon derived from an ester group, the peak of carbon derived from the ester group (COO) was determined by peak-dividing a peak appearing at +4.0 to 4.2 eV from the main peak derived from CH or C—C in C1s. By calculating the ratio of the peak area to all elements, the carbon amount (atomic %) derived from an ester group is determined. More specifically, C1s is composed of five components: a component derived mainly from CHx, C—C, C=C or C—S, a component derived mainly from C—O or C—N, a component derived from a π-π* satellite, a component derived from C=O, and a component derived from COO. Therefore, peak division is performed with five components. The component derived from COO is a peak appearing at +4.0 to 4.2 eV from the main peak of CHx or C—C (around 285 eV). The peak area ratio of each component was calculated while being rounded off from the first decimal place. The amount of carbon (atom %) of C1s was multiplied by the peak area ratio of the component derived from COO. When the peak area ratio was 0.4% or less as a result of peak division, the peak was considered undetectable, and discarded.

The amount of the hydrophilic polymer on the inner surface of the hollow fiber membrane was calculated in accordance with the calculation formula from the measured value obtained by XPS.

Measurement Example 4

Pressure Loss

As shown in the FIG., a roller pump 21 and a pressure gauge 31 were connected to an inlet 41, and a supply bag 11 was connected at the tip next to the roller pump 21. A channel including a roller pump 22 was connected to a filtrate discharge port 43 and a waste liquid bag 13 was connected to the tip of the channel. In addition, a pressure gauge 32 and a recovery bag 12 were connected to an outlet 42.

Next, in order to remove air in a hollow fiber membrane module 51, a phosphate buffer solution (PBS) was added in the supply bag 11, and the solution was fed at a flow rate of 2 L/min by the roller pump 21 until bubbles were not discharged from the outlet 42, so that priming was performed. Thereafter, a pressure loss in the module was calculated from the numerical values indicated by the pressure gauges 31 and 32.

Measurement Example 5

PAC-1 Reaction Rate

The measurement specimen was divided into two specimens. A sample obtained by mixing the specimen with an anti-CD42a antibody, an anti-CD42b antibody, an anti-CD62P antibody and PAC-1 (hereinafter, referred to as sample A) and a sample obtained by adding PMA to sample A in a final concentration of 0.2 µM (hereinafter, referred to as sample B) were prepared. First, with sample A, a co-positive region was formed into a gate for platelets using fluorescent labels of CD41a and CD42b in addition to a gate of a scattered light pattern in a flow cytometer. Next, the gatdd platelet fraction was developed with a fluorescent label of PAC-1 and a fluorescent label of anti-CD62P, and a positive gate was set nearest to each of points where the negative and positive ratios were 100% and 0%. With this setting fixed, sample B was measured instead of sample A, and the ratio of platelets measured in the positive gates of both PAC-1 and the anti-CD62P antibody was determined as a PAC-1 reaction rate.

Measurement Example 6

Annexin Positive Ratio and Total Number of Platelets

The annexin positive ratio was measured in the following manner using a flow cytometer (e.g. FACSVerse from BD Biosciences). First, the platelet suspension liquid before flowing into the module is sampled, and set as a measurement specimen (before treatment). Next, by a roller pump or the like, the platelet suspension liquid is caused to flow from the inlet of the module at 2 L/min and pass through the module, and the platelet suspension liquid flowing out from the outlet is sampled, and used as a measurement specimen (after treatment). A sample obtained by mixing the measurement specimen with an anti-CD41a antibody (BD Pharmingen, 555467) and an anti-CD42b antibody (BD Pharmingen, 555473) (hereinafter, referred to as sample A), and a sample obtained by further mixing Annexin V (BD Horizon, 560506) and Annexin buffer (BD Pharmingen, 556454) with sample A (hereinafter, referred to as sample B) are prepared. When the sample has a high concentration, the sample may be diluted at an appropriate dilution ratio with the Annexin buffer. First, with sample A, a co-positive region was formed into a gate for platelets using fluorescent labels of CD41a and CD42b in addition to a gate of a scattered light pattern in a flow cytometer in measurement with the flow cytometer. From the number measured in the platelet gate, the total number of platelets can be calculated in accordance with the following equation.

total number of platelets (number)=measured value in platelet gate (number)÷measured volume (L)×dilution ratio×volume of platelet suspension liquid (L)

Next, the gated platelet fraction is developed with a fluorescent label of Annexin V, and a positive gate is set at each of boundaries where the negative and positive ratios are 100% and 0%. With this setting fixed, sample B was measured instead of sample A, and the ratio of platelets measured in the positive gate was determined as an annexin-positive ratio of each specimen.

Measurement Example 7

Turn-to-Annexin-Positive Ratio, Platelet Recovery Ratio

A platelet suspension liquid obtained by adding 10% of an ACD-A liquid (TERUMO Corporation) to a 16 L of an incubation liquid containing incubated platelets was provided as a measurement specimen (liquid before treatment), and the number of platelets in the liquid before treatment, the annexin positive ratio and the PAC-1 reaction rate were measured.

Priming was performed as in Measurement Example 4, the contents of the supply bag 11 were changed to the platelet suspension liquid (liquid before treatment), and the recovery bag 12 was emptied. At the same time, feeding of the liquid at 500 mL/min with the roller pump 21 and at 400 mL/min with the roller pump 22 was started at the same time, and the platelet suspension liquid was concentrated. After the platelet incubation suspension liquid (liquid before treatment) in the supply bag 11 was eliminated, both the pumps were stopped, PBS was added in the supply bag 11 again, and the liquid was fed at 500 mL/min for 1 minute with the roller pump 21.

After completion of feeding of the liquid, the recovery bag 12 was sealed at the end, and separated from the circuit. After the recovery bag was reverted to mix the liquid several times, the liquid was sampled from the recovery bag 12, and the number of platelets, the annexin-positive ratio and the PAC-1 reaction rate were measured as the measurement specimen (liquid after treatment).

The turn-to-annexin positive ratio was determined by subtracting the annexin-positive ratio of the measurement specimen (liquid before treatment) from the annexin-positive ratio of the measurement specimen (liquid after treatment).

In addition, the ratio of the total number of platelets after concentration where the total number of platelets before concentration was 100% was calculated as a platelet recovery ratio.

Example 1

A mixture including 15 parts by mass of Udel (registered trademark) Polysulfone (P3500 from Solvay), 8 parts by mass of polyvinylpyrrolidone (PVP) (K90 from ISP), 75 parts by mass of dimethylacetamide (DMAC) and 2 parts by mass of water was mixed and dissolved at 90° C., and then kept at a temperature of 50° C. to obtain a membrane formation stock solution. In addition, 30 parts by mass of PVP (K30 from ISP) was added to a mixed solution including 80 parts by mass of DMAC and 20 parts by mass of water, and the mixture was mixed and dissolved to obtain a core liquid.

Using an orifice-type double cylindrical die having an outer diameter of 1.0 mm and an inner diameter of 0.7 mm, the membrane formation stock solution and the core liquid were simultaneously discharged from the outside cylinder and the inside cylinder, respectively, caused to pass through a 70 mm-long dry portion set at 30° C., and immersed in a coagulation bath at 90° C., which contained a mixed solution including 85 parts by mass of water and 15 parts by mass of DMAC, so that the mixture was solidified. Further the solidified product was washed with warm water in warm water bath at 80° C., and then wound around a reel frame to obtain a hollow fiber membrane in a wet state. When the membrane formation rate was set to 40 ram/min, the inner diameter of the hollow fiber membrane was 300 μm, and the thickness of the hollow fiber membrane was 80 μm.

The obtained hollow fiber membrane in a wet state was subdivided by cutting the hollow fiber membrane to a length of 0.4 m, and immersed in a warm water bath at 90° C. for 50 minutes to be washed with warm water, and was then dried at 100° C. for 10 hours, and further heated at 170° C. for 5 hours by a dry heat dryer to crosslink PVP, thereby obtaining a hollow fiber membrane. The average pore diameter, the water permeability, and the abundance ratio of hydrophilic polymer (PVP) on the inner surface of the obtained hollow fiber membrane were calculated in accordance with the above-described measurement examples, respectively.

From the obtained hollow fiber membrane, a hollow fiber membrane module was prepared in the following manner. First, 5243 hollow fiber membranes obtained as described above were bundled and inserted into a cylindrical casing having an inner diameter of 44 mm and a length of 220 mm, immersed in a 60% glycerin aqueous solution at an end, and dried at 40° C. for 3 days. Subsequently, the ends of the hollow fiber membranes were sealed with a potting agent composed of a polyurethane resin, the potting agent was cut along a direction parallel to the cross-section of the case so that that the hollow fiber membranes were opened outward at both sides, and a header having one port (inlet and outlet) having a cross-sectional area of 2.1 cm$^2$ was attached to both sides. Hot water (3.5 L) at 80° C. was poured at 500 mL/min into the casing packed with the hollow fiber membranes, so that the hollow fiber membranes were washed, and water (2 L) at ordinary temperature was then further poured into the casing at 500 mL/min to wash the hollow fiber membranes. After washing, a 1000 ppm aqueous solution of a vinyl pyrrolidone-vinyl acetate copolymer (VA 64; BASF SE) with 0.1 mass % ethanol dissolved therein was filled, and irradiated with 25 kGy of a γ ray from the outside of the case, so that VA 64 was fixed on the surface of the hollow fiber membrane by radiation irradiation crosslinking treatment to prepare a module having an effective length of 195 mm.

Example 2

Except that the steps including the step of performing washing with water at ordinary temperature, and the preceding steps were carried out, but the subsequent VA64 adding step was not carried out, the same procedure as in Example 1 was carried out to prepare a module.

Example 3

A module was prepared by the same method as in Example 1 except that the module case was cut to change the case length to ½ of the original length (effective length: 101.5 mm).

In the results of Example 3, the turn-to-annexin-positive ratio shown in Table 1 is as poor as 19%. However, this is an apparent result which is caused because the ratio of the total cross-sectional area (X) of the hollow fiber membrane to the total membrane area (Z) of the hollow fiber membrane exceeds 0.0004, so that the platelet recovery ratio decreases. The total cross-sectional area (X) of hollow fiber membranes have an influence on the linear velocity of the liquid passing through the inside of the hollow fiber membrane (membrane intracavity passage linear velocity), and the total membrane area (Z) of hollow fiber membranes has an influence on the linear velocity of the liquid passing from the inside to the outside of the hollow fiber membrane (membrane surface passage linear velocity). When the membrane surface passage linear velocity is increased with respect to the membrane intracavity passage linear velocity, a cake layer with platelets stacked on the surface of the hollow fiber membrane is easily formed. It is considered that since at this time, the cake layer is formed by normal annexin-negative platelets, recovered platelets include a relatively large number of annexin-positive platelets, leading to an apparent increase in turn-to-annexin-positive ratio.

In fact, the number of annexin-positive platelets in evaluation in Example 3 was $3.4 \times 10^9$ before passage through the module and $2.8 \times 10^9$ after passage through the module, which indicates that the number of annexin-positive platelets was slightly reduced by concentration. Even if annexin-positive platelets partially remain and exist in a hollow fiber membrane between normal platelets, the number of such annexin-positive platelets is small, and therefore from this result, it can be said that concentration using the module of Example 3 hardly increased the absolute number of annexin-positive platelets.

Comparative Example 1

A module was prepared by the same method as in Example 1 except that the header of the module case was changed to a tuer lock-type header having one port (inlet and outlet) having a cross-sectional area of 0.8 cm$^2$.

Comparative Example 2

A module was prepared by the same method as in Comparative Example 1 except that the module case was cut to change the case length to ½ of the original length (effective length: 101.5 mm).

Comparative Example 3

A mixture including 15 parts of polymethyl methacrylate (para-styrenesulfonic acid/cationic polymer=3/2; hereinafter referred to as "PMMA") and 85 parts of a dimethyl sulfoxide/glycerin mixed liquid (dimethylsulfoxide/glycerin=85/15) was dissolved at 120° C., and then kept at a temperature of 105° C. to prepare a membrane formation stock solution. In addition, a mixture including 93 parts of dimethylsulfoxide and 7 parts of water was used as a core liquid.

Using an orifice-type double cylindrical die having an outer diameter of 0.9 mm and an inner diameter of 0.65 mm, the membrane formation stock solution and the core liquid were simultaneously discharged from the outside cylinder and the inside cylinder, respectively, caused to pass through a 100 mm-long dry portion set at 30° C., and immersed in a coagulation bath at 90° C., which contained a mixed solution including 90 parts of water and 10 parts of dimethyl sulfoxide, so that the mixture was solidified. Further the solidified product was washed with warm water in warm bath at 80° C., a 75 mass % glycerin aqueous solution was then added, and the mixture was wound around a reel frame to obtain a hollow fiber membrane. When the membrane formation rate was set to 50 mm/min, the inner diameter of the hollow fiber membrane was 300 μm, and the thickness of the hollow fiber membrane was 90 μm.

Using the obtained hollow fiber membrane, a module was prepared by the same method as in Comparative Example 1.

Table 1 shows the material, the average pore diameter and the water permeability of the hollow fiber membranes prepared in the examples and comparative examples, and the total cross-sectional area (Y1) of inlets, the total cross-sectional area (Y2) of outlets, the total cross-sectional area (X) of hollow fiber membranes, the total membrane area (Z) of hollow fiber membranes, X/Y1, X/Y2, X/Z, and the pressure loss of incubated platelet concentration modules prepared using the hollow fiber membranes of the examples and comparative examples, and the results of measurement performed in accordance with various evaluation and measurement examples for the concentrated incubated platelets.

42: Outlet
43: Discharge port
51: Casing
52: Header
53: Header

The invention claimed is:

1. An incubated platelet concentration module comprising: a plurality of hollow fiber membranes each having pores with an average pore diameter of 2 μm or less on a surface of the hollow fiber membrane packed in a casing having at least one inlet for supplying an incubated platelet suspension liquid before concentration into the inside of the hollow fiber membranes and at least one outlet for letting out the concentrated incubated platelet suspension liquid from the inside of the hollow fiber membranes, wherein a value (X/Y1) obtained by dividing a total cross-sectional area (X) of the plurality of hollow fiber membranes by a total cross-sectional area (Y1) of the at least one inlet is 4.0 or less, wherein the total cross-sectional area (X) of the hollow fiber membranes is the sum of cross-sectional areas of the plurality of hollow fiber membranes appearing in a cross-section obtained by cutting the incubated platelet concentration module in a direction perpendicular to the fiber axis direction of the hollow fiber membranes and the cross-sectional area of the hollow fiber membrane is an area of an inner circle of the hollow fiber membrane cut into a round shape and is calculated by the following equation:

hollow fiber membrane cross section=$\pi$(hollow fiber membrane inner diameter/2)$^2$, and the cross-sectional area (Y1) of the at least one inlet is an area of a

TABLE 1

| | | Unit | Example 1 | Example 2 | Example 3 | Comparative Example 1 | Comparative Example 2 | Comparative Example 3 |
|---|---|---|---|---|---|---|---|---|
| Hollow fiber membrane | Material | | Polysulfone | Polysulfone | Polysulfone | Polysulfone | Polysulfone | PMMA |
| | Average pore diameter | μm | 0.66 | 0.66 | 0.66 | 0.66 | 0.66 | 3.4 |
| | Water permeability | mL/hr/Pa/m$^2$ | 100 | 94 | 100 | 100 | 100 | 29 |
| | Abundance ratio of hydrophilic polymer | mass % | 52.1 | 29.6 | 53.9 | 53.2 | 54.2 | — |
| Module | Total cross-sectional area (Y1) of inlets | cm$^2$ | 2.1 | 2.1 | 2.1 | 0.8 | 0.8 | 0.8 |
| | Total cross-sectional area (Y2) of outlets | cm$^2$ | 2.1 | 2.1 | 2.1 | 0.8 | 0.8 | 0.8 |
| | Total cross-sectional area (X) of hollow fiber membranes | cm$^2$ | 3.8 | 3.8 | 3.8 | 3.8 | 3.8 | 3.8 |
| | Total membrane area (%) of hollow fiber membranes | cm$^2$ | 9600 | 9600 | 5000 | 9600 | 5000 | 9600 |
| | X/Y1 | | 1.8 | 1.8 | 1.8 | 4.8 | 4.8 | 4.8 |
| | X/Y2 | | 1.8 | 1.8 | 1.8 | 4.8 | 4.8 | 4.8 |
| | X/Z | | 0.0004 | 0.0004 | 0.00076 | 0.0004 | 0.00076 | 0.0004 |
| | Pressure loss | kPa | 5.0 | 5.4 | 4.5 | 30 | 29 | 30 |
| Evaluation results | turn-to-annexin-poxitive ratio | % | 2.5 | 6.3 | 19 | 15 | 30 | 20 |
| | Platelet recovery ratio | % | 87 | 81 | 26 | 75 | 20 | 50 |
| | PAC-1 reaction rate (before concentration) | % | 74 | 76 | 74 | 74 | 73 | 74 |
| | PAC-1 reaction rate (after concentration) | % | 74 | 72 | 69 | 68 | 62 | 66 |

DESCRIPTION OF REFERENCE SIGNS

11: Supply bag
12: Recovery bag
13: Waste liquid bag
21: Roller pump
22: Roller pump
31: Pressure gauge
32: Pressure gauge
41: Inlet cross-section obtained by cutting the narrowest part of the inlet perpendicularly to the flow direction, and a value (X/Z) obtained by dividing the total cross-sectional area (X) of the plurality of hollow fiber membranes by a total membrane area (Z) of the plurality of hollow fiber membranes is 0.0004 or less, wherein the total membrane area (Z) of hollow fiber membranes is the sum of the inner surface areas of the hollow fiber membranes packed in the incubated platelet concentration module, and is calculated from the following equation when the hollow fiber membranes are uniform:

total membrane area of hollow fiber membranes=inner surface area of hollow fiber membrane×number of hollow fiber membranes, wherein the total membrane area (Z) of the hollow fiber membranes is 0.1 m² or more and 1 m² or less, and the inner surface area of hollow fiber membrane is calculated from the following equation:

inner surface area of hollow fiber membrane=π×(hollow fiber membrane inner diameter×effective length), wherein the effective length is the length obtained by subtracting the length of a part, on which a potting material is deposited, from the total length of the hollow fiber membrane packed in the incubated platelet concentration module, wherein a hydrophilic polymer is carried on the inner surface of the hollow fiber membrane, the hydrophilic polymer including one or more polymers selected from the group consisting of polyvinyl pyrrolidone (PVP), a copolymer of vinyl pyrrolidone and vinyl acetate, and a copolymer of vinyl acetate and vinyl caprolactam.

2. The incubated platelet concentration module according to claim 1, wherein a value (X/Y2) obtained by dividing said total cross-sectional area (X) of the plurality of hollow fiber membranes by a total cross-sectional area (Y2) of the at least one outlet for letting out concentrated incubated platelet suspension liquid passing through the inside of the hollow fiber membranes is 4.0 or less, wherein the cross-sectional area (Y2) of the at least one outlet for letting out concentrated incubated platelet suspension liquid passing through the inside of the hollow fiber membranes is an area of a cross-section obtained by cutting the narrowest part of the outlet for letting out concentrated incubated platelet suspension liquid passing through the inside of the hollow fiber membranes perpendicularly to the flow direction.

3. The incubated platelet concentration module according to claim 1, wherein a pressure loss in supply of the liquid from the inlet to the outlet at a flow rate of 2 L/min is 10 kPa or less, wherein the pressure loss in the incubated platelet concentration module is determined by a first pressure gauge provided immediately before the inlet and a second pressure gauge provided immediately after the outlet of the incubated platelet concentration module, wherein when a liquid before treatment is fed through the incubated platelet concentration module at a flow rate of 2 L/min, the first pressure gauge measures a pressure on an inlet side of the incubated platelet concentration module and the second pressure gauge measures a pressure on the outlet side of the incubated platelet concentration module, and the pressure loss is determined from the following equation:

pressure loss=pressure on inlet side−pressure on outlet side.

4. The incubated platelet concentration module according to claim 1, wherein the hollow fiber membrane has a water permeability of 30 mL/hr/Pa/m² or more.

5. The incubated platelet concentration module according to claim 1, wherein the hollow fiber membrane is a polysulfone-based hollow fiber membrane.

6. A method for producing a platelet preparation, the method comprising the step of concentrating incubated platelets using the incubated platelet concentration module according to claim 1, wherein a concentrated platelet suspension liquid is produced by performing cross-flow in which an incubation liquid containing incubated platelets is caused to flow in from the inlet of the incubated platelet concentration module, and the liquid is discharged from the outlet at the outside of the hollow fiber membranes.

* * * * *